(12) United States Patent
Talib et al.

(10) Patent No.: US 8,950,617 B2
(45) Date of Patent: Feb. 10, 2015

(54) NON-PENETRATIVE BLOOD CONTAINER AND APPARATUS FOR VACUUMING THE SAME

(75) Inventors: Abd. Rahim Bin Abu Talib, Selangor (MY); Mohd. Saleh Yahaya, Selangor (MY); Mohd. Nazim Abdul Rahman, Selangor (MY); Ummi Noor Nazahiah Binti Abdullah, Selangor (MY); Siti Aishah Adam, Selangor (MY)

(73) Assignee: Universiti Putra Malaysia, Selangor Darul Ehsan (MY)

( * ) Notice: Subject to any disclaimer, the term of this patent is extended or adjusted under 35 U.S.C. 154(b) by 320 days.

(21) Appl. No.: 13/547,304

(22) Filed: Jul. 12, 2012

(65) Prior Publication Data

US 2014/0018700 A1   Jan. 16, 2014

(51) Int. Cl.
   *A61J 1/14*   (2006.01)

(52) U.S. Cl.
   USPC ........... 220/202; 220/255; 600/573; 141/65

(58) Field of Classification Search
   CPC ...... A61J 1/065; A61J 1/1406; A61B 5/1438; A61B 5/15003; A61B 5/150213; A61B 5/150259; A61B 5/150351; A61B 5/150274
   USPC ............... 220/202, 233–234, 255; 600/573
   See application file for complete search history.

(56) References Cited

U.S. PATENT DOCUMENTS

| | | | | |
|---|---|---|---|---|
| 3,850,174 A | * | 11/1974 | Ayres | 604/415 |
| 3,852,194 A | * | 12/1974 | Zine, Jr. | 210/789 |
| 4,935,020 A | * | 6/1990 | Broden | 604/411 |
| 4,967,919 A | * | 11/1990 | Earhart | 215/247 |
| 4,982,740 A | * | 1/1991 | Broden | 600/573 |
| 5,306,270 A | * | 4/1994 | Macartney et al. | 604/415 |
| 5,313,969 A | * | 5/1994 | Hsieh | 600/577 |
| 5,527,513 A | * | 6/1996 | Burns | 422/549 |
| 5,575,375 A | | 11/1996 | Sandusky et al. | |
| 5,860,937 A | * | 1/1999 | Cohen | 600/576 |
| 6,497,325 B1 | * | 12/2002 | DiCesare et al. | 210/516 |
| 6,672,345 B2 | | 1/2004 | Sarstedt | |
| 6,793,885 B1 | * | 9/2004 | Yokoi et al. | 422/401 |
| 6,946,100 B2 | * | 9/2005 | Yokoi et al. | 422/415 |
| 7,959,866 B2 | * | 6/2011 | Crawford et al. | 422/550 |
| 8,052,944 B2 | * | 11/2011 | Kacian et al. | 422/570 |
| 8,057,762 B2 | * | 11/2011 | Kacian et al. | 422/570 |
| 8,530,231 B2 | * | 9/2013 | Nakae et al. | 435/307.1 |
| 2003/0108447 A1 | * | 6/2003 | Yokoi et al. | 422/58 |
| 2004/0052682 A1 | * | 3/2004 | Yokoi et al. | 422/58 |
| 2005/0000962 A1 | * | 1/2005 | Crawford et al. | 220/23.87 |
| 2005/0065454 A1 | * | 3/2005 | Manoussakis | 600/576 |
| 2010/0323437 A1 | * | 12/2010 | Nakae et al. | 435/307.1 |

FOREIGN PATENT DOCUMENTS

EP   2111795 A1   10/2009
MY   PI 2010700039   6/2010

* cited by examiner

*Primary Examiner* — Nicolas A Arnett
(74) *Attorney, Agent, or Firm* — Muncy, Geissler, Olds & Lowe, P.C.

(57) ABSTRACT

A non-penetrative vacuum blood container for storing blood sample, the non-penetrative vacuum blood container comprises: (a) a cap (1) having a number of air passages (4) at its inner wall and ridges (5) at is outer wall; (b) an enclosure (2) which includes enclosure head (8), enclosure neck (9) and enclosure chamfer (10); and (c) a tube (3) for storing blood sample; wherein the air passages (4) further includes enclosure stopper (7) close to opening (6) of the cap (1); and wherein an enclosure opening (11) is provided at the enclosure head (8).

10 Claims, 4 Drawing Sheets

NON-PENETRATIVE BLOOD CONTAINER AND APPARATUS FOR VACUUMING THE SAME

FIELD OF INVENTION

The present invention generally relates to a non-penetrative vacuum blood container and apparatus for vacuuming the same.

BACKGROUND OF THE INVENTION

Blood samples and other biological fluid specimens are normally taken and analyzed in hospital and clinical situations for various medical purposes. Some blood samples are taken and analyzed for laboratory test. Collection, handling, testing and using these samples typically requires the use of various medical testing instruments. As the blood and fluid specimens are usually collected in a standard sized vacuum collection tubes, the medical instruments used to test the samples are designed to accommodate these standard sized vacuum collection tubes.

Conventional vacuum blood collection tubes or containers used for storing blood sample in laboratory test are usually elongated cylindrical containers having one end closed by closure device tightly sealed thereon. This is to maintain the vacuum condition inside the tube until the time for use and to avoid any contamination of the contents which would distort the analytical result. Accordingly, the conventional vacuum blood containers are of glass or plastic tubes which sealed with partial vacuum inside by rubber stopper or enclosure, so that air pressure inside the tube is negative, less than the normal environment.

The current typical process of producing the vacuum in the tube is by needle punching technique. The air is withdrawn from the tube individually to provide vacuum condition inside the tube using penetrative technique. A needle is used to withdraw air through the tube enclosure to provide vacuum condition. The vacuum pressure in the tube is set to be at specified level in order to withdraw the exact amount of the blood sample need in medical practices. The whole process of producing the vacuum in the tube is time consuming and the penetration technique may resulted air leak in the enclosure. Hence, this will reduced the capability of the tube to withdraw sufficient amount of blood sample required.

Blood sample taken from patient which used needle attached in front to the tube is known in the art. Accordingly, low vacuum pressure inside the tube allows the blood to flow into the tube easily with correct amount required.

Typically, the vacuum blood container comes in variety of sizes and shapes depending on the amount of blood sample needed. The inner side of the tub also has different coatings of gel, chemicals and power, which depend on the required blood test.

Many inventions related to the vacuum blood container have been disclosed, for example, U.S. Pat. No. 5,575,375 and EP 2111795. However, they are related only to vacuum blood container with penetrative process technique.

It is also known that vacuuming is an essential process for producing vacuumed blood container tubes. The vacuum condition inside the blood container needs to be maintained until the blood sample is used for analysis. The existing method of producing vacuum blood container tube is using penetrating vacuum process wherein needle is inserted through rubber enclosure to draw the air from the tube. An example of this kind of process is disclosed in U.S. Pat. No. 6,672,345. The process described hoe the tube is evacuated by a pump where the pump is assembled with needle. This needle is inserted into the enclosure to assist the pump draws out the air through the needle itself. When the required vacuum pressure is achieved, the needle is pulled out from the enclosure. However this technique is only applicable for penetrating blood container tube.

In view of the foregoing, it is desirable to provide a non-penetrative vacuum blood container and apparatus for vacuuming said non-penetrative vacuum blood container. Accordingly, features of constructions, combination of elements and arrangement of parts of the preferred embodiments will be exemplified in the detailed description.

SUMMARY OF THE INVENTION

The present invention to a non-penetrative vacuum blood container and apparatus for vacuuming the same. Accordingly, the non-penetrative vacuum blood container for storing blood sample, the non-penetrative vacuum blood container comprises: (a) a cap having a number of air passages at its inner wall and ridges at is outer wall; (b) an enclosure which includes enclosure head, enclosure neck and enclosure chamfer; and (c) a tube for storing blood sample; wherein the air passages further includes enclosure stopper close to opening of the cap; and wherein an enclosure opening is provided at the enclosure head.

Accordingly, the air passages of the cap provide air flow effectively from the tube. The air passages provide half-close assembly condition to the cap prior to vacuum process. It will be appreciated that the enclosure stopper of the air passages prevents enclosure from fall-off.

In the preferred embodiment, the opening of the cap is provided on the top of the cap to allow easy access for blood withdrawal. The ridges at is outer wall of the cap provide better grip condition for the user. It will be appreciated that the enclosure opening of the enclosure head allows easy fitting of the enclosures into the cap.

Accordingly, the enclosure neck of the enclosure provides sufficient seal between the cap and tube during the vacuum process. The enclosure chamfer provides easy movement for the enclosure to be inserted into the tube during full-capped condition. Preferably, the enclosure is a rubber material which acts as a seal to provide sufficient vacuum condition to the tube.

Accordingly, the tube is designed to have a hemispherical tube bottom and tube wall is preferably has a smooth inner and outer surfaces.

In another preferred embodiment, a vacuum chamber machine for vacuuming the non-penetrative vacuum blood container tubes, the vacuum chamber machine comprises: (a) a vacuum chamber cylinder acts as a main body of the vacuum chamber machine, wherein the vacuum chamber cylinder is attached to a sliding plate; (b) a pusher attached to a pneumatic cylinder 1 and to be used as an actuator to full-capped the non-penetrative vacuum blood container tubes; (c) a pneumatic cylinder 2 is provided and is used as a system to move the sliding plate that allow movement of the vacuum chamber cylinder to close and open; (d)a blood container jig designed to load the half-capped non-penetrative vacuum blood container tubes; and to be loaded on a jig locator under the vacuum chamber cylinder; and (e) a control panel serves as main control system of the vacuum chamber machine.

Accordingly, the machine is driven by electrical power and pneumatic systems. It will be appreciated that a pair of side plates is further provided to serve as a guide to move the sliding plate. The sliding plate is used to hold the vacuum chamber cylinder so that to move the vacuum chamber cylinder forward and backward; to close and open the vacuum chamber.

Accordingly, the blood container jig allows number of non-penetrative vacuum blood container tubes per vacuuming process.

Accordingly, the control panel includes a start and stop buttons, a digital pressure sensor, main power isolator and a socket for vacuum pump. If desired, the control panel is further provided with a buzzer that serve as a device to indicate the completion of the process or as an alarm an emergency.

BRIEF DESCRIPTION OF THE DRAWINGS

The accompanied drawings constitute part of this specification and include exemplary or preferred embodiments of the invention, which may be embodied in various forms. It should be understood, however, the disclosed preferred embodiments are merely exemplary of the invention. Therefore, the figures disclosed herein are not to be interpreted as limiting, but merely as the basis for the claims and for teaching one skilled in the art of the invention.

In the appended drawings:

FIGS. 4b-4c are a front view and side view of the vacuum chamber machine of FIG. 4a;

DETAILED DESCRIPTION OF THE PREFERRED EMBODIMENTS

Figure 1:
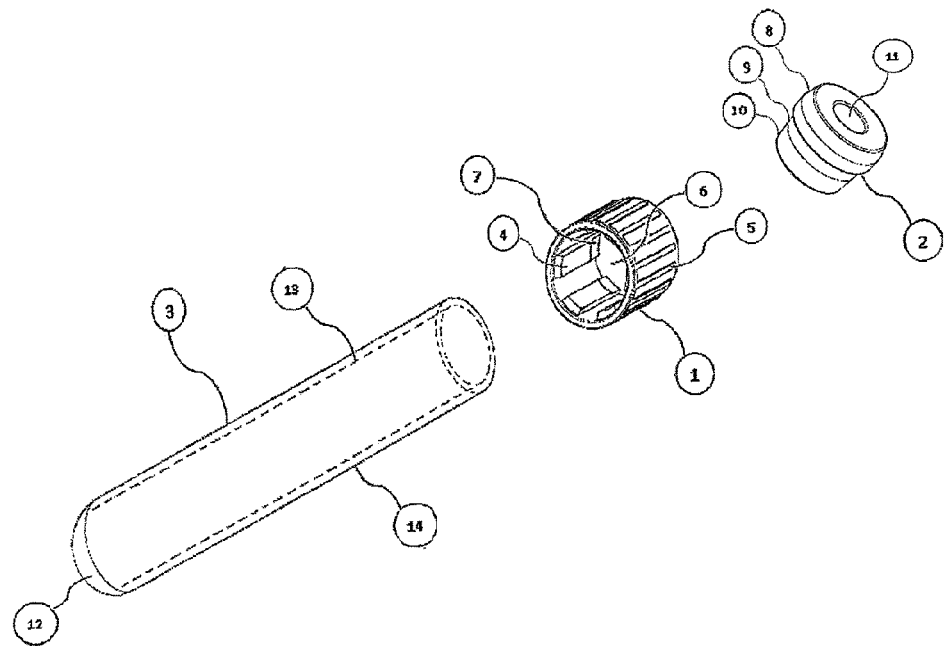
FIG. 1 is diagrammatic exploded view of a non-penetrative vacuum blood container in accordance with preferred embodiment of present invention.

A detailed description of preferred embodiments of the invention is disclosed herein. It should be understood, however, the disclosed preferred embodiments are merely exemplary of the invention, which may be embodied in various forms. Therefore, the details disclosed herein are not to be interpreted as limiting, but merely as the basis for the claims and for teaching one skilled in the art of the invention.

A non-penetrative vacuum blood container and apparatus for vacuuming the same according to the preferred embodiments of the present invention will now be described in accordance to the accompanying drawings FIGS. 1 to 5c, both individually and in any combination thereof.

In the preferred embodiment, the non-penetrative vacuum blood container generally includes a cap (1), an enclosure (2) and a tube (3). Accordingly, the cap (1) is provided with a number of air passages (4) at its inner wall and ridges (5) at is outer wall. The air passages (4) provide air flow effectively from the tube (3).

Accordingly, the air passages (4) are designed to have enclosure stopper (7) close to opening (6) of the cap (1) to prevent enclosure (2) from fall-off. Moreover, the air passages (4) also provide half-close assembly condition to the cap (1) prior to vacuum process. It will be appreciated that the opening (6) is provided on the top of the cap (1) to allow easy access for blood withdrawal. The ridges (5) are provided on outer wall surface of the cap (1) so that to provide better grip condition for the user.

The enclosure (2) is preferably designed to have three main sections. The three main sections of the enclosure (2) are enclosure head (8), enclosure neck (9) and enclosure chamfer (10). An enclosure opening (11) is provided at the enclosure head (8). Accordingly, the enclosure opening (11) of the enclosure head (8) allows easy fitting of the enclosures (2) into the cap (1). It will be appreciated that the enclosure neck (9) is designed to provide sufficient seal between the cap (1) and tube (3) during the vacuum process. The enclosure chamfer (10) is designed purposely to allow easy movement for the enclosure (2) to be inserted into the tube (3) during full-capped condition. It will be appreciated that the enclosure (2) can be specifically made of, but not limited to special rubber materials which can be act as a seal to provide sufficient vacuum condition to the tube (3).

Preferably, the tube (3) is designed to have a hemispherical tube bottom (12) and tube wall is preferably has a smooth inner (13) and outer (14) surfaces.

Figure 2:
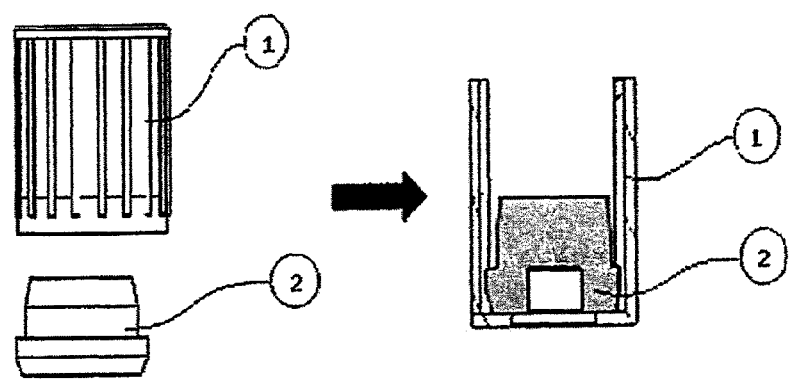
FIG. 2 illustrating an assembly of a cap and an enclosure in accordance with preferred embodiment of the present invention.

In assembly, the enclosure (2) is inserted into cap (1). Accordingly, as shown in FIG. 2, the enclosure (2) is pushed firmly into the cap (1) until it is fit sited at the end of the cap (1). Particularly, the enclosure (2) is securely positioned at the enclosure stopper (7). The cap (1) and the enclosure (2) will then be placed on top opening of the tube (3) (FIG. 3a).

Figures 3A, 3B, 3C:
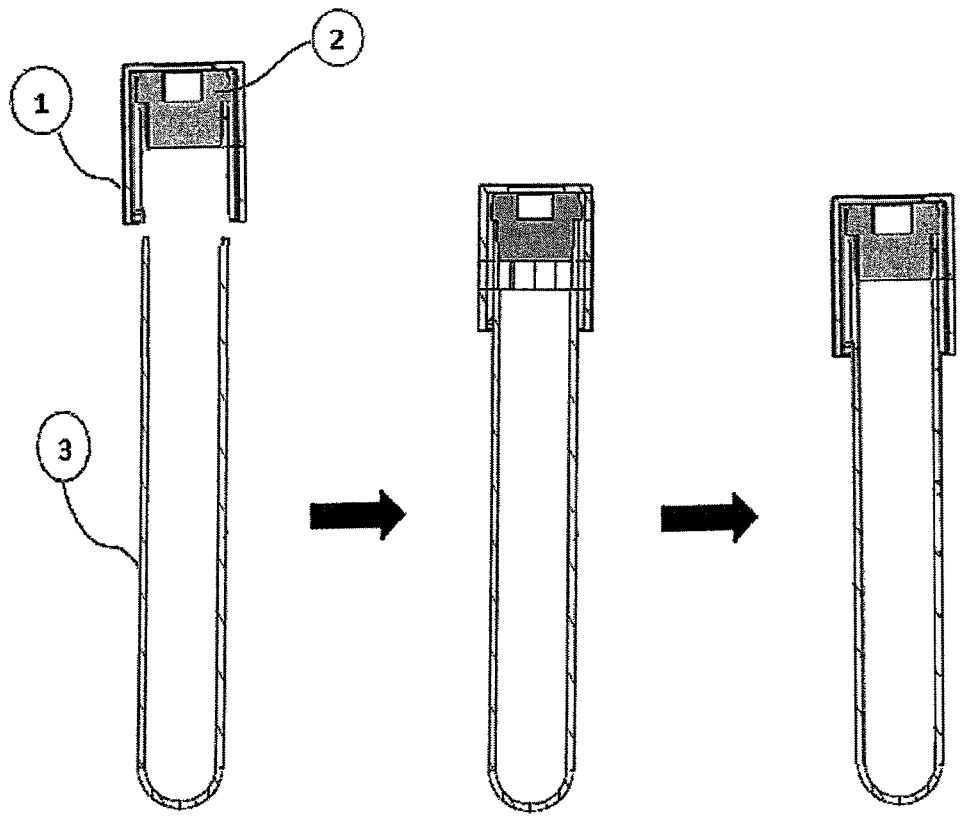
FIGS. 3a-3c illustrating the non-penetrative vacuum blood container where the cap and enclosure are placed on top of the tube; to which the non-penetrative vacuum blood container is in half-capped condition and in fully capped condition respectively.

It will be appreciated that prior to vacuuming process, the cap (1), enclosure (2) and tube (3) of the non-penetrative vacuum blood container are assembled in half-capped condition as shown in FIG. 3b. The non-penetrative vacuum blood container will then be placed inside a custom made vacuum chamber cylinder of a vacuum chamber machine which will be described in details hereinafter. The cap (1) serves as to hold the enclosure (2) in its place to prevent from fall-off and to allow a minimum clearance for vacuum process to occur. When the vacuum process started, a mechanism inside the chamber will closed the enclosure (2) and the cap (1) fully onto the tube (3).

When vacuum pressure is achieved at a required level, the tube (3) of the non-penetrative vacuum blood container will be fully closed by a capping system in the vacuum chamber. The enclosure (2) will act as a stopper of the opening end of the tube (3) and serve as closure device for air holes at the tube body. This is to ensure that no vacuum is leaking from the tube (3) and other vacuum blood container parts. The vacuum blood container will be moved out from the vacuum chamber for other process deemed suitable.

Figure 4A:
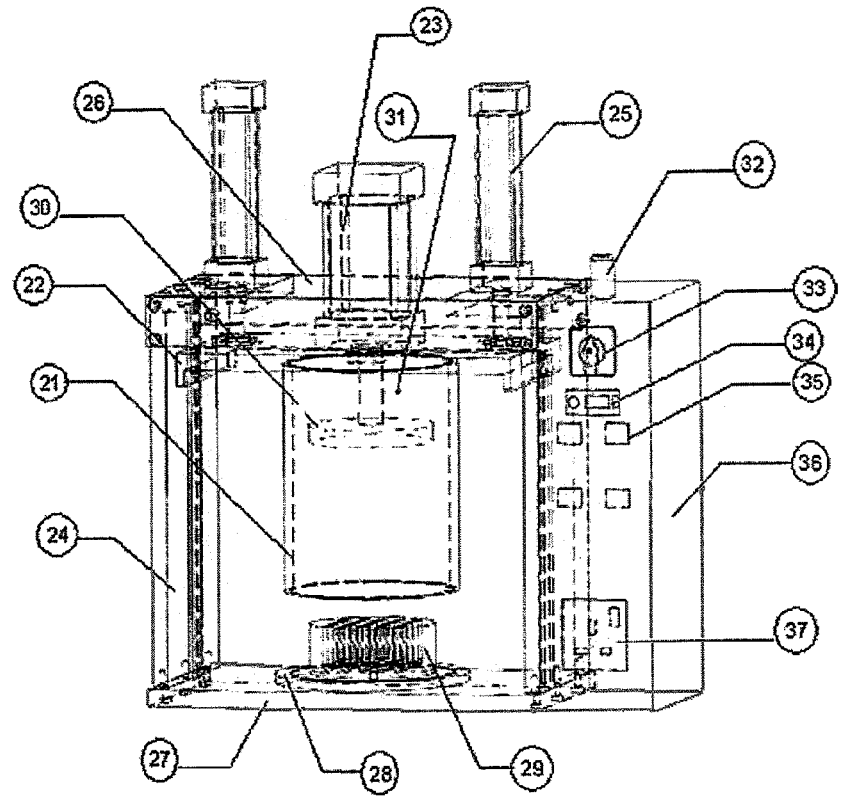
FIG. 4a is a diagrammatic see-through view of a vacuum chamber machine and its component thereof in accordance with another preferred embodiment of the present invention.
Figures 4B, 4C:
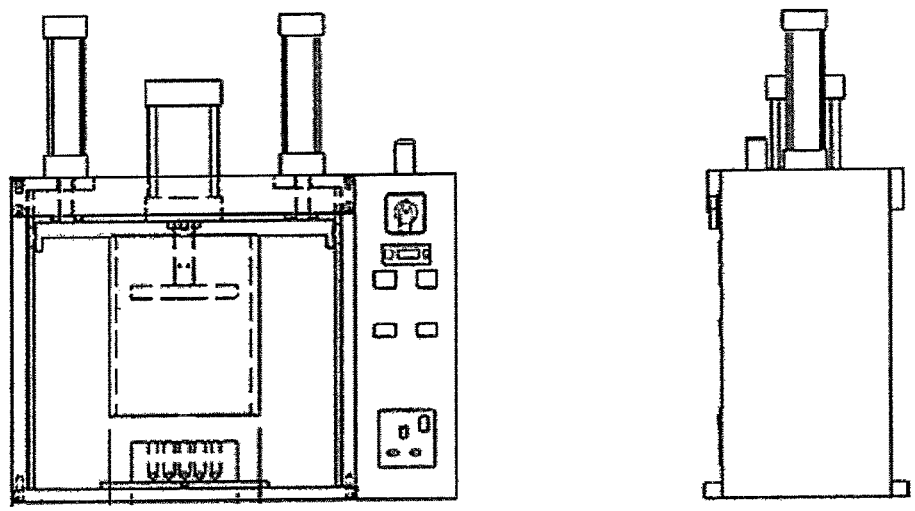
Figure 5A:
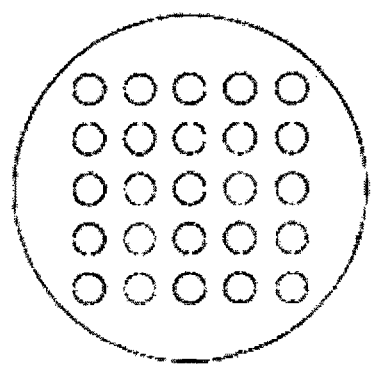
FIGS. 5a-5c are plan view, perspective view and side view of a blood container jig of the preferred embodiment of the present invention.
Figure 5B:
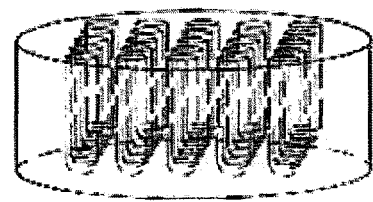
Figure 5C:
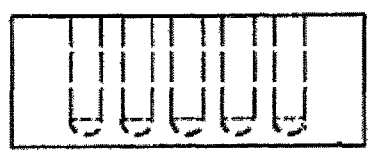

Referring now to FIGS. 4a-4c, the vacuum chamber machine for vacuuming blood container tubes is shown. Accordingly, the vacuum chamber machine is used to vacuum the non-penetrative vacuum blood container tube. Preferably, the machine is driven by electrical power and includes pneumatic systems.

In the preferred embodiments, the vacuum chamber machine includes a vacuum chamber cylinder (21) which attached to a sliding plate (22) on a top part of the vacuum chamber cylinder (21). Accordingly, the vacuum chamber cylinder (21) acts as a main body of the vacuum chamber machine. It will be appreciated that a pusher (30) is provided and located inside the vacuum chamber cylinder (21). Accordingly, the pusher (30) is attached to a pneumatic cylinder 1 (23). The pusher (30) is used as an actuator to full-capped the non-penetrative vacuum blood container tubes by means of the pneumatic cylinder 1 (23). A pneumatic cylinder 2 (25) is provided and is used as a system to move the sliding plate (22) which attached to the vacuum chamber cylinder (21) as well as the pneumatic cylinder 1 (23). Accordingly, the pneumatic cylinder 2 (25) is provided to allow movement of the vacuum chamber cylinder (21) to close and open; and the pneumatic cylinder 1 (23) is provided to move the pusher (30) inside the vacuum chamber cylinder (21) up and down. It will be appreciated that a pair of side plates (24) is provided to serve as a guide to move the sliding plate (22).

By moving the sliding plate (22), the vacuum chamber cylinder (21) is moved forward and backward; to close and open the vacuum chamber. The sliding plate (2) is used to hold the vacuum chamber cylinder (21). It will be appreciated that a blood container jig (29) is designed to load the half-capped non-penetrative vacuum blood container tube as shown in FIG. 3a, and to be loaded on a jig locator (28) under the vacuum chamber cylinder (21). The blood container jig (29) allows number of non-penetrative vacuum blood container tubes per vacuuming process. A supporting plate (26) is provided and is used to support device structure by putting said plate in front and back of the structure to make the overall structure firm. It will be appreciated that main control system of the vacuum chamber machine is a control panel (26). Accordingly, the control panel (26) includes a start and stop buttons (35), a digital pressure sensor (34), main power isolator (33) and a socket for vacuum pump (37). A buzzer (32) is preferably provided and located on the control panel (26) as a device to indicate the completion of the process or as an alarm if an emergency occurred.

The detailed step-by-step procedure of the vacuum chamber machine will be described now. First, a vacuum pump is connected to the vacuum chamber machine by inserting its plug into the socket for vacuum pump (37) and the main power isolator (33) is turn ON. It will be appreciated that a desired pressure is set on the digital pressure sensor (34). The process begins with placing the half-capped non-penetrative vacuum blood container tube (FIG. 3a) into the blood container jig (29). Preferably, as shown is FIGS. 5a-5c, capacity of the blood container jig (29) is, but not limited to twenty five tubes. The blood container jig (29) filled with the non-penetrative vacuum blood container tubes will then be loaded on the jig locator (28) under the vacuum chamber cylinder (21) when it is in open position. The jig locator (28) serves to firmly hold the blood container jig (29). It will be appreciated that the a base plate (27) is provided to which the jig locater (28) is attached, to serve as the base of the machine structure.

Next, the start button (35) is pressed to start the machine operation. Accordingly, after start button (35) is pressed, the vacuum chamber cylinder (21) will be automatically pushed down to close the chamber tightly followed by vacuum pump will be started to operate. When the pressure reaches the desired level, the pusher (30) in the vacuum chamber cylinder (21) will be automatically moved downward to fully-capped the non-penetrative vacuum blood container tubes, and then actuated backward to its original position. The buzzer (32) will sound to indicate the process is completed. Next step is to press stop button (35) so that to enable the pressure to be returned to atmospheric pressure. The vacuum chamber cylinder (21) is then lifted up and the blood container jig (29) will full-capped non-penetrative vacuum blood container tubes can be now unloaded and conveyed to other processes as deemed suitable.

While embodiments of the invention have been illustrated and described, it is not intended that these embodiments illustrate and describe all possible forms of the invention. Rather, the words used in the specification are words of description rather than limitation and various changes may be made without departing from the scope of the invention.

The invention claimed is:

1. A non-penetrative vacuum blood container for storing blood sample, the non-penetrative vacuum blood container comprises:
    a) a cap (1) having a number of air passages (4) at its inner wall and ridges (5) at is outer wall;
    b) an enclosure (2) which includes enclosure head (8), enclosure neck (9) and enclosure chamfer (10); and
    c) a tube (3) for storing blood sample;
    wherein the air passages (4) further include an enclosure stopper (7) close to an opening (6) of the cap (1);
    wherein an enclosure opening (11) is provided at the enclosure head (8);
    wherein the enclosure head extends out from the tube, the enclosure neck contacts the tube and the enclosure chamfer extends into the tube; and
    wherein the air passages (4) provide air flow effectively from the tube (3) during a vacuum process.

2. A non-penetrative vacuum blood container according to claim 1, wherein the air passages (4) provide a half-close assembly condition to the cap (1) prior to the vacuum process.

3. A non-penetrative vacuum blood container according to claim 1, wherein the enclosure stopper (7) prevents the enclosure (2) from fall-off.

4. A non-penetrative vacuum blood container according to claim 1, wherein the opening (6) is provided on the top of the cap (1) to allow easy access for blood withdrawal.

5. A non-penetrative vacuum blood container according to claim 1, wherein the ridges (5) provide better grip condition for the user.

6. A non-penetrative vacuum blood container according to Claim. 1, wherein the enclosure opening (11) of the enclosure head (8) allows fitting of the enclosures (2) into the cap (1).

7. A non-penetrative vacuum blood container according to .Claim 1, wherein the enclosure neck (9) provides sufficient seal between the cap (1) and tube (3) during the vacuum process.

8. A non-penetrative vacuum blood container according to claim 1, wherein the enclosure chamfer (10) provides movement for the enclosure (2) to be inserted into the tube (3) during full-capped condition.

9. A non-penetrative vacuum blood container according to claim 1, wherein the enclosure (2) is a rubber material which acts as a seal to provide sufficient vacuum condition to the tube (3).

10. A non-penetrative vacuum blood container according to claim 1, wherein the tube (3) is designed to have a hemispherical tube bottom (12) and tube wall is preferably has a smooth inner (13) and outer (14) surfaces.

* * * * *